United States Patent
Miyamoto

(10) Patent No.: US 8,574,600 B2
(45) Date of Patent: Nov. 5, 2013

(54) POROUS PARTICLES AND COSMETICS

(75) Inventor: Masafumi Miyamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 1603 days.

(21) Appl. No.: 10/544,678

(22) PCT Filed: Feb. 3, 2004

(86) PCT No.: PCT/JP2004/001053
§ 371 (c)(1),
(2), (4) Date: Aug. 4, 2005

(87) PCT Pub. No.: WO2004/069907
PCT Pub. Date: Aug. 19, 2004

(65) Prior Publication Data
US 2006/0204527 A1    Sep. 14, 2006

(30) Foreign Application Priority Data
Feb. 4, 2003 (JP) .................. 2003-026670

(51) Int. Cl.
*A61K 9/00* (2006.01)
(52) U.S. Cl.
USPC ...................... 424/400; 424/70.11
(58) Field of Classification Search
None
See application file for complete search history.

(56) References Cited

U.S. PATENT DOCUMENTS

| | | | |
|---|---|---|---|
| 5,231,119 A * | 7/1993 | Govoni et al. | 523/221 |
| 5,316,774 A * | 5/1994 | Eury et al. | 424/501 |
| 5,888,930 A * | 3/1999 | Smith et al. | 504/359 |
| 6,080,818 A * | 6/2000 | Thakker et al. | 525/240 |
| 6,300,468 B1 * | 10/2001 | Bretz et al. | 528/497 |

FOREIGN PATENT DOCUMENTS

| | | |
|---|---|---|
| EP | 0 183 103 | 6/1986 |
| EP | 0 519 342 | 12/1992 |
| JP | 57098205 | 6/1982 |
| JP | 60-76505 | 5/1985 |
| JP | 60-184004 | 9/1985 |
| JP | 5-194620 | 8/1993 |
| JP | 25502621 | 8/1996 |
| JP | 10-505116 | 5/1998 |
| JP | 11-92599 | 4/1999 |
| JP | 2000-516973 | 12/2000 |
| JP | 2003-128827 | 5/2003 |
| WO | 97/20884 | 6/1997 |
| WO | 98/55540 | 12/1998 |

OTHER PUBLICATIONS

English translation of JP 60-184044 (1985); Japanese document provided by Applicant.*
English translation of JP 11-92599 (1999)); Japanese document provided by Applicant.*
For the non-English documents cited above, the English language equivalents were considered.

* cited by examiner

*Primary Examiner* — Nissa Westerberg
(74) *Attorney, Agent, or Firm* — Oblon, Spivak, McClelland, Maier & Neustadt, L.L.P.

(57) ABSTRACT

The invention provides porous particles, a process for producing the porous particles, and cosmetics comprising the porous particles. The porous particles of the invention have an average particle diameter of 75 μm or less, based on polyethylene resin having a crystallization degree of 70% or more. The porous particles further comprise an active ingredient. The process for producing the porous particles, comprises mixing polyethylene resin having a crystallization degree of 70% or more, and a low-molecular weight compound having a melting point lower than the softening temperature (or melting point) of the polyethylene resin, with each other at a temperature not lower than the softening temperature (or melting point) of the polyethylene resin, then spraying the mixture into a gaseous phase or a solvent at a temperature at which the viscosity of the mixture becomes 600 mPa·s or less, and removing the low-molecular weight compound from the resulting particles.

14 Claims, No Drawings

POROUS PARTICLES AND COSMETICS

FIELD OF THE INVENTION

The present invention relates to porous particles useful in cosmetics, a process for producing the same, and cosmetics containing the same.

BACKGROUND OF THE INVENTION

Conventionally, porous particles have been developed. JP-B 2550262 discloses an oil absorber containing an organic acid metal salt and an oil-absorbing crosslinked polymer, containing porous particles which swell by absorbing a large amount of oil, are excellent in an ability to retain absorbed oil, and significantly improve the rate of absorption of oil.

As a process for producing non-swelling porous particles, JP-A (W) 2000-516973 discloses porous spherical particles obtained by melt-mixing polypropylene with dichlorobenzole or amyl acetate for dissolving the polymer, then spray-cooling the mixture, and removing the solvent in a later step.

SUMMARY OF THE INVENTION

The present invention relates to porous particles having a small particle diameter of 75 μm or less on the average, which are preferable as cosmetics with oil absorptivity, the porous particles further containing an active ingredient, a process for producing the same, and cosmetics containing the same.

The present invention relates to porous particles having an average particle diameter of 75 μm or less, containing polyethylene resin having a crystallization degree of 70% or more as the main component. The present invention also relates to the porous particles further containing an active ingredient and cosmetics containing the porous particles. The present invention also relates to a process for producing porous particles, which includes mixing polyethylene resin having a crystallization degree of 70% or more, and a low-molecular weight compound having a melting point lower than the softening temperature (or melting point) of the polyethylene resin with each other at a temperature not lower than the softening temperature (or melting point) of the polyethylene resin, then spraying the mixture into a gaseous phase or a solvent at a temperature at which the viscosity of the mixture is 600 mPa·s or less, and removing the low-molecular weight compound from the resulting particles.

The present invention relates to cosmetics containing the porous particles described above or porous particles obtained by the process described above and another cosmetic ingredient.

The present invention relates to use of the porous particles described above or porous particles obtained by the process described above as cosmetics.

DETAILED DESCRIPTION OF THE INVENTION

The porous particles in JP-B 2550262 supra are a swelling type and thus change their particle shape upon absorption of oil, and therefore the feeling thereof on the skin is not satisfactory. Further, there is a problem that the production process is not easy, thus increasing the cost.

In JP-A (W) 2000-516973 supra, there is a problem that the solvent is limited, the particles having a particle diameter of 100 μm or less are hardly made porous, and their porosity is low.

[Porous Particles]

The porous particles of the present invention are based on polyethylene resin having a crystallization degree of 70% or more and preferably a molecular weight of 1000 or more, and may contain other components, for example inorganic and organic pigments, coloring materials such as organic dyes etc., surfactants, silicone compounds, and antioxidants such as metal oxides etc. insofar as the effect of the present invention is not hindered.

From the viewpoint of suppressing gritty feel and frictional feel, the average particle diameter of the porous particles is 75 μm or less, preferably 0.1 to 75 μm, more preferably 0.3 to 40 μm. This average particle diameter is the weight-average particle diameter of a suspension of the particles in alcohol measured by a laser diffraction particle-diameter distribution measuring instrument (LS-230 model manufactured by Coulter, Inc.) at room temperature (20° C.)

The shape of the porous particles of the present invention is preferably spherical from the viewpoint of the excellent feel of the spherical particles on the skin and less aggregation of the particles.

The void volume of the porous particles of this invention is preferably 5 to 95%, more preferably 30 to 70%. The void volume is determined by mercury porosimetry described later. The pores forming voids may be in the form of a communicating hole having the respective pores connected with one another.

The porous particles of the present invention have an ability to absorb oil, and upon incorporation of an active ingredient, they function for example as a release agent for releasing the active ingredient by melting the active ingredient at the temperature of skin.

[Polyethylene Resin]

The polyethylene resin in the present invention is an ethylene polymer. The production process is not particularly limited. The polyethylene resin used may be modified or unmodified, but should have a crystallization degree of 70% or more. The degree of modification should be regulated in such a range that the degree of crystallization is kept at 70% or more. The molecular weight is preferably 1000 or more, more preferably 2000 or more. The upper limit of the molecular weight is not particularly limited, but for regulating the viscosity at the time of spraying, the molecular weight is preferably 20000 or less, more preferably 10000 or less. The molecular weight can be determined as viscometric average molecular weight by viscometry. The degree of crystallization is 70% or more, preferably 75% or more, more preferably 80% or more, and the upper limit is preferably 95% or less, from the viewpoint of easy availability of the material. As the degree of crystallization is increased, pores have smaller diameters even if the void volume is the same, and thus the resulting polyethylene resin is excellent in extendibility as described later. The degree of crystallization can be determined by an X-ray diffraction method under the following measurement conditions.

<Measurement Conditions of the X-Ray Diffraction Method>

Apparatus: RINT 2500, manufactured by Rigaku Denki Co., Ltd.

Radiation source: Cu
Tube current: 300 mA
Tube voltage: 50 kV
Scan speed: 2°/min.

The melting point of the polyethylene resin is preferably 80° C. or more, more preferably 120° C. or more. The upper limit is not particularly limited, but is preferably 200° C. or less in order to prevent pyrolysis of the low-molecular weight compound in the production process described later. The melting point of the polyethylene resin can be measured by JIS K0064:1992.

[Low-Molecular Weight Compound]

The low-molecular weight compound used in the present invention is a compound having a molecular weight of preferably 50 to 1000, more preferably a compound having a molecular weight of 100 to 500.

The low-molecular weight compound has a melting point lower than the softening temperature (or melting point) of the polyethylene resin, and the difference between the softening temperature (or melting point) of the polyethylene resin and the melting point of the low-molecular weight compound is preferably 10° C. or more, more preferably 20° C. or more, still more preferably 30° C. or more, in order to facilitate the production process described later. In respect of easy production, the difference in melting point may be 100° C. or less. Preferably, the low-molecular weight compound has a melting point of 25° C. or more and is in a solid form at room temperature (25° C.). The melting point of the low-molecular weight compound can be measured by JIS K0064:1992.

The low-molecular weight compound is preferably hydrophobic for excellent compatibility with the polyethylene resin. The hydrophobic low-molecular weight compound includes a compound having 12 or more carbon atoms, silicone, and derivatives thereof.

Examples of the low-molecular weight compound used in the present invention includes branched, linear or cyclic higher alcohols such as lauryl alcohol, cetyl alcohol, stearyl alcohol, oleyl alcohol, behenyl alcohol, lanoline alcohol, hydrogenated lanoline alcohol, isostearyl alcohol, cholesterol etc.; branched or linear higher fatty acids such as myristic acid, palmitic acid, stearic acid, arachidonic acid etc.; branched or linear alkyl ethers such as distearyl ether etc.; hydrocarbon compounds such as paraffin, vaseline, microcrystalline wax etc.; naturally occurring lipid and oil compounds such as squalane, squalene, mink oil, jojoba oil, carnauba wax, beeswax, candelilla wax, lanoline etc.; terpene compounds such as 1-menthol; ester compounds such as myristyl myristate, myristyl stearate, isopropyl myristate, isopropyl lanoline fatty ester, myristyl myristate, octyl dodecyl myristate, glycerin trimyristate, cholesteryl isostearate etc.; silicone, for example cyclic silicone such as octyl methyl cyclotetrasiloxane, dodecamethyl cyclohexasiloxane etc., linear silicone such as dimethyl polysiloxane, methyl phenyl polysiloxane etc., and amino-modified silicone, polyether-modified silicone, methyl phenyl polysiloxane, fatty acid-modified silicone, alcohol-modified silicone, alkoxy-modified silicone, epoxy-modified silicone, fluorine-modified silicone, cyclic silicone, alkyl-modified silicone etc., as well as derivatives thereof.

The compounding ratio of the low-molecular weight compound is preferably 5 to 1900 parts by weight, more preferably 43 to 233 parts by weight, relative to 100 parts by weight of the polyethylene resin. In this range, porous particles having sufficient porosity can be obtained.

[Active Ingredient]

Various uses of the active ingredient are assumed, and thus its properties are not particularly limited, but the melting point is preferably not higher than the softening point (or melting point) of the polyethylene resin, more desirably lower than 50° C. in respect of releasability on the skin. An active ingredient soluble in sebaceous matter and sweat is also desirable even if its softening point is 50° C. or higher. The melting point of the active ingredient can be measured according to JIS K0064:1992.

The active ingredient includes an emollient on the skin, a humectant having a water-retaining action arising from the specific structure, a protective agent acting as a protective membrane on the skin and hair, an antioxidant, an agent for reinforcing and repairing cuticles, a cooling agent, an antiperspirant, a blood circulation promoter etc.

Such compounds include those mentioned as the low-molecular weight compound, and are not particularly limited insofar as they have a low-molecular weight. Among these compounds, mention is made particularly of naturally occurring compounds such as squalane, squalene etc., and silicone such as cyclic silicone and derivatives thereof. Other preferable examples include vitamins such as vitamin A, vitamin E, panthenol, pantothenyl ethyl ether etc.; ceramide and substances having a similar structure thereto (for example, substances represented by the general formulae (1) and (2) in JP-A 5-213731), 1-menthol, etc. The active ingredient may be a mixture of these substances.

The active ingredient can be used as it is, without removing the low-molecular weight compound from the polyethylene resin in the process of producing the porous particles. Alternatively, after the porous particles are produced, the active ingredient can be contained in the porous particles by absorption.

The compounding ratio of the active ingredient is preferably 5 to 1900 parts by weight, more preferably 43 to 233 parts by weight, relative to 100 parts by weight of the polyethylene resin.

[Process for Producing the Porous Particles]

To obtain the porous particles of the present invention, the polyethylene resin according to the present invention and the low-molecular weight compound having a melting point lower than the softening temperature (or melting point) of the polyethylene resin are mixed with each other at a temperature not lower than the softening temperature (or melting point) of the polyethylene resin. At the time of mixing, the polyethylene resin and the low-molecular weight compound are compounded in such a ratio that the amount of the low-molecular weight compound is preferably 5 to 1900 parts by weight, more preferably 43 to 233 parts by weight, based on 100 parts by weight of the polyethylene resin. In addition, solid and liquid components, for example inorganic and organic pigments, coloring materials such as organic dyes etc., surfactants, silicone compounds, and antioxidants such as metal oxides etc. can be melted in, or mixed with, the mixture. Then, the porous particles are obtained from this mixture by a spray cooling method or a solvent cooling method shown below, preferably the spray cooling method.

<Spray Cooling Method>

Preferably, the above mixture is sprayed into a gaseous phase preferably at 5 to 50° C. by using a rotating disk atomizer or one fluid nozzle or two or more fluid nozzles, and particles solidified by cooling are recovered. Preferably, the mixture together with compressed gas is sprayed into a gases phase by using a plurality of fluid (two or more fluids) nozzles. The compressed gas used as fluid may be compressed air or compressed nitrogen preferably at $9.8 \times 10^4$ Pa or more, more preferably at $9.8 \times 10^4$ to $29.4 \times 10^4$ Pa. This gas is preferably heated at the spraying temperature in order to prevent clogging in a nozzle upon cooling, thus enabling continuous production of the particles.

From the viewpoint of achieving excellent spraying, the spraying temperature is a temperature at which the viscosity of the mixture of the polyethylene resin and the low-molecular weight compound becomes preferably 600 mPa·s or less, more preferably 300 mPa·s or less, still more preferably 100 mPa·s or less. Although there is no particular lower limit, the lower limit is preferably a temperature at which the viscosity becomes 5 mPa·s or more.

Then, the low-molecular weight compound is removed from the resulting particles. The low-molecular weight compound is removed preferably with a solvent at a temperature lower than the softening temperature (or melting point) of the polyethylene resin, preferably a temperature of 20° C. or more, more preferably at a temperature equal to or higher than the melting point of the low-molecular weight compound, from the viewpoint of the efficiency of removal. The low-molecular weight compound may be removed under reduced pressure.

The solvent is added in an amount of preferably 1 to 100 parts by weight relative to 1 part by weight of the particles obtained by spraying, and is mixed at the above-mentioned temperature to eluate the low-molecular weight compound. This washing can be conducted repeatedly to give the porous particles.

The solvent is not particularly limited insofar as it dissolves the low-molecular weight compound but does not dissolve the polyethylene resin. Examples of the solvent include lower alcohols such as ethanol, isopropanol etc.; lower ketone compounds; hydrocarbon solvents, for example aliphatic hydrocarbons such as hexane, heptane, dodecane, cyclohexane, methyl cyclohexane, isooctane, hydrogenated triisobutylene etc. and aromatic hydrocarbons such as benzene, toluene, xylene, ethyl benzene etc.; and silicone solvents such as octamethyl cyclotetrasiloxane, decamethyl cyclopentasiloxane etc.

<Solvent Cooling Method>

The solvent cooling method is a method which involves injecting the mixture dropwise in the form of spray mist into a solvent, instead of spraying the mixture into a gaseous phase. The solvent is preferably a solvent such as glycerin having a high boiling point and not compatible with the polyethylene resin and the low-molecular weight compound. The dropping temperature is a temperature at which the viscosity becomes preferably 600 mPa·s or less, more preferably 300 mPa·s or less, still more preferably 100 mPa·s or less, and is preferably not higher than the boiling point of the solvent. Although there is no particular lower limit, the lower limit is preferably a temperature at which the viscosity becomes 5 mPa·s or more. Thereafter, the particles can be obtained by cooling the solvent. The method of removing the low-molecular weight compound from the resulting particles is the same as in the spray cooling method.

[Cosmetics]

In the cosmetics of the present invention, the content of the porous particles according to the present invention can be selected suitably depending on the object of the cosmetics, and is not particularly limited, but is preferably 0.1 to 50 wt %, more preferably 1 to 30 wt %.

The form of the cosmetics of this invention is not particularly limited, and the cosmetics may be water-in-oil or oil-in-water emulsified cosmetics, oil cosmetics, spray cosmetics, stick-type cosmetics, aqueous cosmetics, sheet-shaped cosmetics, and gelled cosmetics. The type of the cosmetics of this invention is not particularly limited, and the cosmetics of this invention include skin cosmetics such as a pack, foundation, lipstick, lotion, cold cream, hand cream, skin detergent, softening cosmetics, nutrient cosmetics, astringent cosmetics, whitening cosmetics, wrinkle-care cosmetics, anti-aging cosmetics, cleansing cosmetics, antiperspirants and deodorant; and hair cosmetics such as a shampoo, rinse, treatment, hairdressing, hair tonic etc.

Preferably, the cosmetics of this invention further contain an alcohol. The alcohol includes C1-6 monohydric or polyhydric alcohols such as ethanol, glycerin, 1,3-butylene glycol, propylene glycol and sorbitol. In particular, a monohydric alcohol, particularly ethanol is preferable. The amount of the alcohol incorporated is preferably 5 to 30% by weight in the cosmetics of this invention, particularly preferably 2 to 50 times as high as the weight of the porous particles according to this invention.

Depending on the form, type etc. of the cosmetics, other conventional components can be further incorporated as cosmetic components into the cosmetics of this invention in such a range that the effect of this invention is not hindered.

Such cosmetic components include e.g. extender pigments such as mica, talc, sericite, kaolin, nylon powder, polymethylsilyl sesquioxane and barium sulfate; inorganic pigments such as titanium oxide, zinc white and iron oxide; powders whose surface was rendered hydrophobic by treating these powders with silicone, metal soap or N-acyl glutamic acid; hydrocarbons such as solid or liquid paraffin, microcrystalline wax, vaseline, ceresin, ozokerite and montan wax; vegetable or animal fats and oils or wax, such as olive, ozokerite, carnauba wax, lanoline and spermaceti; fatty acids or esters thereof such as stearic acid, palmitic acid, oleic acid, glycerin monostearate, glycerin distearate, glycerin monooleate, isopropyl myristate, isopropyl stearate and butyl stearate; higher alcohols such as cetyl alcohol, stearyl alcohol, palmityl alcohol and hexyl dodecyl alcohol; adsorbents or thickening agents such as cationic cellulose, carboxybetaine type polymer and cationic silicone; polyhydric alcohols having a moisture retention action, such as glycol and sorbitol; efficacious components such as whitening agent, analgesic antiinflammatory agents, anti-itching agents, sterilizing disinfectants, astringents, skin softening agents and hormones; water; surfactants; W/O or O/W type emulsifying agents; emulsifying agents for silicone oil, such as polyether-modified silicone, polyether alkyl-modified silicone and glyceryl ether-modified silicone; thickening agents such as methyl cellulose, ethyl cellulose, carboxymethyl cellulose, polyacrylic acid, tragacanth, agar and gelatin; and other components such as emulsion stabilizer, chelating agents, UV protecting agents, pH adjusting agents, preservatives, coloring matters and perfumes.

The porous particles of the present invention can be produced inexpensively and can give dry and powdery feel as an absorber of sebaceous matter. Further, the composite particles containing the active ingredient are excellent in feel during application, and can give an excellent feel on the skin for a long time.

EXAMPLES

The following examples show embodiments of the present invention. The Examples are set forth for merely illustrative purposes, and not intended to restrict the present invention.

In the Examples, the term "%" refers to wt % unless otherwise specified. The viscosity at the time of spraying is a value measured at 60 rpm for 1 minute by a Brookfield viscometer (rotor having a measurement scale in the range of 5 to 95 was used). The melting point is a value measured according to JIS K0064:1992. The void volume was calculated from pore volume per one gram of particles by using a mercury porosimeter Pore Sizer 9320 manufactured by Shimadzu Corporation. The void volume (%) can be calculated according to the following equation:

$$\text{Void volume}(\%) = [(\text{volume of pores in particles})/(\text{volume of pores in particles} + (\text{true specific gravity of particles})^{-1})] \times 100$$

Example 1

Mitsui HiWax HW-200P (molecular weight 2000, melting point 122° C., degree of crystallization 87%, manufactured by Mitsui Chemicals, Inc.) as polyethylene resin, and stearic acid (LUNAC S-98, melting point 70° C., manufactured by Kao Corporation) as a low-molecular weight compound, were mixed with each other in a mixing ratio of 30:70 (polyethylene resin: stearic acid) and then melted by heating at 180° C. Then, the melt together with a nitrogen stream at 180° C. was sprayed through 2-fluid nozzles (glass sprayer M type, manufactured by SANSHO) into a gaseous phase at 25° C., cooled therein, and recovered as solid particles. The viscosity at the time of spraying was 40 mPa·s. 5 g of the particles were mixed in 100 ml ethanol at 60° C. and stirred for 2 minutes to extract the stearic acid, and then concentrated under reduced pressure through a 0.8 μm PTFE membrane filter to give spherical porous particles (weight-average particle diameter 20 μm, void volume 70%).

Example 2

Spherical porous particles (weight-average particle diameter 15 μm, void volume 70%) were obtained by conducting the treatment in the same procedure as in Example 1 except that Mitsui HiWax HW-100P (molecular weight 1000, melting point 116° C., degree of crystallization 90%, manufactured by Mitsui Chemicals, Inc.) was used as the polyethylene resin. The viscosity at the time of spraying was 20 mPa·s.

Example 3

Spherical porous particles (weight-average particle diameter 30 μm, void volume 70%) were obtained by conducting the treatment in the same procedure as in Example 1 except that Mitsui HiWax HW-800P (molecular weight 8000, melting point 127° C., degree of crystallization 90%, manufactured by Mitsui Chemicals, Inc.) was used as the polyethylene resin. The viscosity at the time of spraying was 120 mPa·s.

Example 4

Spherical porous particles (weight-average particle diameter 20 μm, void volume 70%) were obtained by conducting the treatment in the same procedure as in Example 1 except that Mitsui HiWax HW-210P (molecular weight 2000, melting point 114° C., degree of crystallization 75%, manufactured by Mitsui Chemicals, Inc.) was used as the polyethylene resin. The viscosity at the time of spraying was 40 mPa·s.

Example 5

Polyethylene/squalane composite particles (weight-average particle diameter 20 μm) were obtained by conducting the treatment in the same procedure as in Example 1 except that squalane (melting point −38° C.) was used as the low-molecular weight compound, and the extraction step was omitted. The viscosity at the time of spraying was 40 mPa·s.

Example 6

1 g oleyl alcohol was mixed with 1 g of the spherical porous particles obtained in Example 1 to give composite particles having oleyl alcohol carried in voids of the porous particles.

Example 7

Spherical porous particles (weight-average particle diameter 20 μm, void volume 70%) were obtained by conducting the treatment in the same procedure as in Example 1 except that Mitsui HiWax HW-220P (molecular weight 2000, melting point 114° C., degree of crystallization 70%, manufactured by Mitsui Chemicals, Inc.) was used as the polyethylene resin. The viscosity at the time of spraying was 40 mPa·s.

Comparative Example 1

Spherical porous particles (weight-average particle diameter 28 μm, void volume 70%) were obtained by conducting the treatment in the same procedure as in Example 1 except that Mitsui HiWax HW-720P (molecular weight 7200, melting point 113° C., degree of crystallization 60%, manufactured by Mitsui Chemicals, Inc.) was used as the polyethylene resin. The viscosity at the time of spraying was 100 mPa·s.

Comparative Example 2

Spherical porous particles (weight-average particle diameter 25 μm, void volume 70%) were obtained by conducting the treatment in the same procedure as in Example 1 except that Mitsui HiWaxNL100P (molecular weight 2400, melting point 110° C., degree of crystallization 54%, manufactured by Mitsui Chemicals, Inc.) was used as the polyethylene resin. The viscosity at the time of spraying was 80 mPa·s.

Comparative Example 3

Spherical porous particles (weight-average particle diameter 20 μm, void volume 70%) were obtained by conducting the treatment in the same procedure as in Example 1 except that polypropylene resin (Mitsui HiWaxNP055, molecular weight 7000, melting point 136° C., degree of crystallization 60%, manufactured by Mitsui Chemicals, Inc.) was used in place of the polyethylene resin. The viscosity at the time of spraying was 40 mPa·s.

Comparative Example 4

Spherical porous particles (weight-average particle diameter 20 μm, void volume 10%) were obtained by conducting the treatment in the same procedure as in Example 1 except that polypropylene resin (Mitsui HiWaxNP055, molecular weight 7000, melting point 136° C., degree of crystallization 60%, manufactured by Mitsui Chemicals, Inc.), was used in place the polyethylene resin, and amyl acetate was used in place of stearic acid, and the mixing ratio by weight (polypropylene resin:amyl acetate) was 20:80. The viscosity at the time of spraying was 20 mPa·s.

Comparative Example 5

Non-porous particles (weight-average particle diameter 20 μm) were obtained by conducting the treatment in the same procedure as in Example 2 except that the low-molecular weight compound was not used, and the extraction step was omitted. The viscosity at the time of spraying was 40 mPa·s.

Comparative Example 6

1 g oleyl alcohol was mixed with 1 g of the particles obtained in Comparative Example 5 to give a mixture of the particles and oleyl alcohol.

Test Example 1

Squalene was dropped gradually into 1 g of the spherical porous particles obtained in each of Examples 1 to 3 or 1 g of the non-porous particles obtained in Comparative Example 5, and the amount of squalene dropped and a change in the viscosity of the kneaded material under kneading with a spatula were observed, and the amount of total squalene dropped until a rapid reduction in viscosity was observed, was determined as the amount of oil absorbed into the particles. The results are shown in Table 1.

TABLE 1

|  | Amount of oil absorbed (ml/g) |
| --- | --- |
| Example 1 | 4.0 |
| Example 2 | 4.0 |
| Example 3 | 4.0 |
| Comparative example 5 | 0.4 |

Test Example 2

The spherical porous particles obtained in Examples 1 to 4 and Comparative Examples 1 to 4 were evaluated for extendibility by the following method, and the feel thereof as cosmetics was evaluated by a specialist. The results are shown in Table 2.

<Evaluation of Extendibility>

A plurality of particles were sandwiched between fingers of the specialist, the fingers were rubbed together, and the state of the particles diffused between the fingers was judged according to the following criteria:

◯: Spread uniformly.
X: Spread unevenly.

TABLE 2

|  | Extendibility | Feel |
| --- | --- | --- |
| Example 1 | ◯ | Feel very dry and powdery |
| Example 2 | ◯ | Feel very dry and powdery |
| Example 3 | ◯ | Feel very dry and powdery |
| Example 4 | ◯ | Feel dry and powdery |
| Example 7 | ◯ | Feel dry and powdery |
| Comparative example 1 | X (aggregated) | Feel slightly gritty |
| Comparative example 2 | X (aggregated) | Feel slightly gritty |
| Comparative example 3 | X (aggregated) | Feel slightly gritty |
| Comparative example 4 | X (aggregated) | Feel slightly gritty |

As is evident from the results in Table 2, the spherical porous particles of the present invention were excellent in extendibility and feel.

Test Example 3

The composite particles obtained in each of Examples 5 to 6 and Comparative Example 6 were applied in a suitable amount onto the inner side of the forearm, and the feel thereof during application was evaluated according to the following criteria Six hours after the application, the feel of the particles was further evaluated. The results are shown in Table 3.

◯: Spread uniformly.
X: Spread unevenly.

TABLE 3

|  | Feel during application | Feel in 6 hours after the application |
| --- | --- | --- |
| Example 5 | ◯ | Feel moist |
| Example 6 | ◯ | Feel moist |
| Comparative example 6 | X (Feel strongly liquid) | Feel moist |

As is evident from the results in Table 3, the composite particles of the present invention were excellent both in feel during application and in feel in 6 hours after application.

| Formulation Example of Cosmetics (Emollient Cream) | |
| --- | --- |
| Stearic acid | 7.5% |
| Cetostearyl alcohol | 1.5 |
| Liquid paraffin | 10.0 |
| Glycerin triisooctanoate | 12.0 |
| Lanolin | 3.0 |
| Cetyl palmitate | 4.0 |
| Monostearic acid polyethylene glycol (EO = 40) | 2.0 |
| Monostearic acid glycerin (self-emulsifiable) | 5.0 |
| Spherical porous particles in Example 1 | 3.0 |
| Preservative/antioxidant | suitable amount |
| Perfume | suitable amount |

Purified water in an amount to adjust the total to 100.0%

The invention claimed is:

1. A process for producing porous particles having an average diameter of 75 μm or less, consisting of mixing a polyethylene resin having a crystallization degree of 70% or more and a low-molecular weight (LMW) compound having a melting point lower than the softening temperature or melting point of the polyethylene resin with each other at a temperature not lower than the softening temperature or melting point of the polyethylene resin, then spraying the mixture into a gaseous phase or a solvent at a temperature at which the viscosity of the mixture is 600 mPa·s or less and removing the low-molecular weight compound from resulting particles,
wherein pores of the porous particles forming voids are in a form of a communicating hole having the respective pores connected with one another, and
the low-molecular weight (LMW) compound is at least one compound selected from the group consisting of myristic acid, palmitic acid, stearic acid, and arachidonic acid.

2. The process according to claim 1, wherein the molecular weight of the polyethylene resin is 1000 to 20000.

3. The process according to claim 1, wherein a ratio of the low-molecular weight compound is 43 to 233 parts by weight relative to 100 parts by weight of the polyethylene resin.

4. The process according to claim 1, wherein the mixture of the polyethylene resin and the LMW compound is mixed with a gas compressed at $9.8 \times 10^4$ Pa or greater, and the mixture is released by spraying using a rotating disk atomizer or at least one fluid nozzle into the gaseous phase or the solvent.

5. The process according to claim 1, wherein the mixture of the polyethylene resin and the LMW compound is released by spraying into the solvent.

6. The process according to claim 1, wherein the LMW compound is removed from the resulting particles by using at least one compound selected from the group consisting of a lower alcohol, a lower ketone compound, a hydrocarbon solvent, and a silicone solvent.

7. The process according to claim 1, wherein the void volume of the porous particles is 30 to 95%.

8. A process for producing porous particles having an average diameter of 75 μm or less, consisting essentially of mixing a polyethylene resin having a crystallization degree of 70% or more and a low-molecular weight (LMW) compound having a melting point lower than the softening temperature or melting point of the polyethylene resin with each other at a temperature not lower than the softening temperature or melting point of the polyethylene resin, then spraying the mixture into a gaseous phase or a solvent at a temperature at which the viscosity of the mixture is 600 mPa·s or less and removing the low-molecular weight compound from resulting particles, wherein pores of the porous particles forming voids are in a form of a communicating hole having the respective pores connected with one another, and the low-molecular weight (LMW) compound is at least one compound selected from the group consisting of myristic acid, palmitic acid, stearic acid, and arachidonic acid.

9. The process according to claim 8, wherein the molecular weight of the polyethylene resin is 1000 to 20000.

10. The process according to claim 8, wherein a ratio of the low-molecular weight compound is 43 to 233 parts by weight relative to 100 parts by weight of the polyethylene resin.

11. The process according to claim 8, wherein the mixture of the polyethylene resin and the LMW compound is mixed with a gas compressed at $9.8 \times 10^4$ Pa or greater, and the mixture is released by spraying using a rotating disk atomizer or at least one fluid nozzle into the gaseous phase or the solvent.

12. The process according to claim 8, wherein the mixture of the polyethylene resin and the LMW compound is released by spraying into the solvent.

13. The process according to claim 8, wherein the LMW compound is removed from the resulting particles by using at least one compound selected from the group consisting of a lower alcohol, a lower ketone compound, a hydrocarbon solvent, and a silicone solvent.

14. The process according to claim 8, wherein the void volume of the porous particles is 30 to 95%.

* * * * *